United States Patent [19]

Ellison et al.

[11] Patent Number: 4,600,800
[45] Date of Patent: Jul. 15, 1986

[54] DOWNFLOW ISOMERIZATION OF EPOXIDES

[75] Inventors: Robert H. Ellison; Peter S. Friend, both of Houston, Tex.

[73] Assignee: Shell Oil Company, Houston, Tex.

[21] Appl. No.: 804,011

[22] Filed: Dec. 3, 1985

[51] Int. Cl.$^4$ .............................................. C07C 35/08
[52] U.S. Cl. .................................... 568/832; 568/833; 502/22
[58] Field of Search ................... 568/832, 833; 502/22

[56] References Cited

U.S. PATENT DOCUMENTS 4,551,566  11/1985  Robson et al. ...................... 568/833
4,564,715  1/1986  Briggs et al. ........................ 568/833

FOREIGN PATENT DOCUMENTS 653351  5/1951  United Kingdom ................ 568/832

OTHER PUBLICATIONS

Klein et al., Dragoco Rep. vol. 18 (1971) pp. 239–243.

Primary Examiner—Werren B. Lone

[57] ABSTRACT

An epoxide is isomerized in the liquid phase in the presence of a solid alumina catalyst and preferably an inert gaseous diluent, the isomerization conducted in the downflow mode.

17 Claims, No Drawings

DOWNFLOW ISOMERIZATION OF EPOXIDES

BACKGROUND OF THE INVENTION

1. Field of the Invention

The present invention relates to the downflow isomerization of an epoxide to the corresponding alcohol in the presence of alumina catalyst.

2. Description of the Prior Art

It is known to isomerize epoxides to alcohols with alumina, e.g. E. Klein and W. Rojahn, *Dragoco Rep.*, 18, 239–243 (1971) in English. In the process of this publication, about 23 times excess of alumina is used relative to the terpinolene-4,8-oxide starting material.

When the applicant tried to use catalytic amounts of alumina, it was found that the alumina catalyst was very rapidly deactivated in the course of the reaction, resulting in long reaction times and large amounts of catalyst to achieve reasonably high conversions.

SUMMARY OF THE INVENTION

The present invention is directed to a process for the isomerization of an epoxide to the corresponding alcohol which comprises isomerizing epoxide in the liquid phase in the presense of a solid alumina catalyst, the isomerization conducted in the downflow (or trickle flow) mode.

The process of the invention, conducted in the downflow (or trickle flow) mode, not only has the advantage of improving the catalyst reactivity but also increases the catalyst lifetime. The water from a competing elimination reaction, which had previously caused catalyst deactivation, is no longer readily absorbed on the alumina, thereby greatly extending the usefulness of the alumina catalyst. Thus, the invention is also directed to a process for increasing the life of a solid alumina catalyst used in the isomerization of an epoxide to the corresponding alcohol which comprises conducting the isomerization in the downflow mode of a liquid epoxide.

The epoxides which can be isomerized by the process of the invention are mono-, di-, tri- and tetra-substituted epoxides known in the art and containing the oxygen atom attached to two adjacent carbon atoms. Preferably, both of these adjacent carbon atoms are not also part of a carbocyclic ring. These epoxides are readily prepared by conventional procedures known in the art for the epoxidation of aliphatic and cycloaliphatic, mono- and non-conjugated polyolefins with e.g. hydrogen peroxide or hydrocarbyl hydroperoxides, preferably in the presence of various metal catalysts.

As examples of the olefins to prepare di-, tri- and tetrahydrocarbyl substituted epoxides, there can be used such substituted diverse materials as:

(a) Aliphatic olefins, such as propylene, butenes, isobutene, hexenes, 4-methyl-2-pentene, etc.;

(b) Cycloolefins, for example, cyclopentene, cyclohexene, cyclooctene, etc.;

(c) Alkyl and alkenyl cycloolefins, for example, methylcyclohexene, methylcyclopentene, vinylcyclohexene;

(d) Compounds having a plurality of olefinic double bonds, unconjugated, for example 1,5-cyclooctadiene, 1,5,9-cyclododecatriene, 1,4-cyclohexadiene, cyclohexadiene;

(e) Terpenes, for example, p-menthadienes such as terpinolene, terpinenes, etc.

For example, the epoxide is a tetra-substituted olefinic epoxide in which one carbon of the olefinic group is part of a carbocyclic ring so that the resulting alcohol function is tertiary and attached to the ring. Preferably, the epoxide is a terpenoid epoxide, i.e. one prepared by epoxidation of a terpene, including monocyclic, bicyclic and acyclic terpenes, for example, an epoxide prepared from epoxidation of a p-menthadiene and, especially terpinolene epoxide.

The epoxide should be essentially dry or free of water to avoid introducing extraneous water into the process.

The isomerization process of the invention is usually conducted in the absence of added solvents for the epoxide because the usual solvents, such as water, alcohols and hydrocarbons, inhibit the reaction.

The isomerization process of the invention is conducted by passing epoxide in the liquid downwardly over a solid alumina catalyst at the desired temperature and pressure in a vacuum or, preferably, an inert atmosphere, until the desired degree of conversion has been completed and recovering the desired alcohol product by conventional techniques, such as distillation, extraction and the like. The process may be conducted as a batch or continuous process.

In the downflow or trickle flow isomerization process the rate of conversion and selectivity to the desired alcohol can vary with the temperature of the reaction under normal pressures. A reaction temperature of about 0°–200° C. can be used, but a temperature in the range of about 70° to about 160° C. and especially about 110° to about 150° C. gives high conversion in a relatively shorter reaction time.

A catalytic amount of alumina is used in the present process. The rate of reaction varies somewhat with the catalyst concentration so that the catalyst concentration can be flexible. For convenience, the alumina is used in an amount of from about 0.5% to about 35% weight based upon the weight of the epoxide, and preferably from about 1% to about 25% by weight and especially from about 5% to about 15% by weight.

Any conventional natural and synthetic alumina catalyst including alpha, chi and gamma aluminas, can be used in the isomerization process of the invention. The catalyst generally has a conventional particulate form as spheres or, preferably, extrudates and the like. The alumina is used in an activated form having acidic sites. If the alumina is not initially in activated form, it can be activated as described later in this application. It has also been found that catalyst activity does vary to some degree with the sodium content of the alumina. An alumina catalyst with a low sodium content is preferred. For example, the sodium content of from about 0 to about 0.5 weight percent based upon the weight of alumina and, preferably from about 0 to about 0.1 weight percent.

The catalyst may be initially inactive or may lose activity after some time of use and can be activated or regenerated by conventional techniques known in the art which lower the water content of the alumina and increase the acidity, such as heating the catalyst at elevated temperatures of above about 90° C., for example, between about 100° C. to about 500° C. and, preferably about 120° C. to about 200° C.

In the preferred embodiment of the invention, an inert gaseous diluent is used in the downflow mode. This results in a three-phase reaction in which the catalyst is the solid phase, the epoxide reactant is the liquid phase and the inert gaseous diluent is the third phase.

This is particularly useful in a continuous process, for example, using a fixed bed reactor, or a batch process, for example, using a circulating (or pump-around) reactor. While any inert gaseous diluent can be used, for convenience, the insert gas is usually nitrogen or a mixture thereof with inert gases such as argon and the like. Since the downflow of inert gaseous diluent is a further aid to increasing the alumina catalyst life, it should be used as dried inert gas so that extraneous water is not introduced into the process. While the presence of some inert gaseous diluent is desirable, it is preferable for higher catalyst activity to employ the inert gaseous diluent at a flow rate of from about 40 to about 500 ml/min and especially at about 100 to 400 ml/min, if the inert gaseous diluent is used on a once-through basis. When it is desired to recycle the inert gaseous diluent, then lower flow rates of about 50 to about 100 ml/min can be used along with a minimal drying of the recycle gas.

The present invention, as described and detailed above, is advantageous as a process to isomerize epoxides in high conversion and good selectivity with lower reaction times.

The product (allylic) alcohols are known in the art and have application in organic synthesis, for example, as intermediates to the corresponding saturated alcohols, unsaturated halides, halosubstituted allyl alcohols, and the like. The alcohols derived by isomerization of epoxides made from terpenes can also have application in the perfumery industry. In particular, terpinene-4-ol is an important constituent of many so-called "essential" oils and has similar utility.

ILLUSTRATIVE EMBODIMENTS

The following Embodiments are presented for the purpose of illustrating the invention and should not be regarded as limiting it in any way.

EMBODIMENTS 1-24

A pump-around reactor was employed which used a 16 inch tube reactor with an internal diameter of ½ inch. A Beckman model 110A solvent metering pump was used to pump terpinolene-4,8-oxide (TPLO). The feed/product vessel was a stirred glass reactor which was nitrogen blanket while the reactor could be under vacuum or nitrogen blanketed. The feed was circulated through the reactor in downflow mode. An alumina catalyst bed of approximately 10 ml was located in the center section of the reactor. A preheating zone filled with glass beads was used. Catalyst activation was performed in the reactor under vacuum by heating to the desired temperature. Samples were removed from the feed/product vessel at appropriate intervals and analyzed by gas chromatography (GC). Numbers from these GC analyses are reported as area percent and are not otherwise calibrated.

TABLE 1

DOWNFLOW ISOMERIZATION OF TERPINOLENE OXIDE[a]

| Embodiment | $N_2$ Flow (ml/min) | TPLO Conv. (%) | Reaction Time (hr) | DPNL (%) |
|---|---|---|---|---|
| 1[b] | none | 99 | 4 | 77 |
| 2[b] | none | 95 | 7 | 75 |
| 3 | 20 | 98 | 3 | 75 |
| 4 | 20 | 98 | 9 | 78 |
| 5 | 50 | 99 | 1.5 | 70 |
| 6 | 50 | 99 | 3 | 73 |
| 7 | 50 | 99 | 3 | 74 |
| 8 | 100 | 99 | 1.5 | 73 |
| 9 | 100 | 99 | 2 | 75 |
| 10 | 100 | 99 | 2.5 | 74 |
| 11 | 100 | 98 | 2 | 74 |
| 12 | 100 | 99 | 2.5 | 74 |
| 13 | 100 | 99 | 3 | 75 |
| 14 | 400 | 99 | 3 | 77 |
| 15 | 400 | 99 | 3 | 76 |
| 16 | 400 | 99 | 3 | 76 |
| 17 | 400 | 99 | 3 | 75 |
| 18[c] | 100 | 100 | 3 | 77 |
| 19[c] | 100 | 100 | 4 | 76 |
| 20[c] | 100 | 100 | 4 | 76 |
| 21[c] | 100 | 99 | 4 | 75 |
| 22[d] | 100 | 99 | 4 | 77 |
| 23[d] | 100 | 99 | 5 | 77 |
| 24[d] | 100 | 99 | 4 | 76 |

[a]Standard conditions: 6 g of KC-300 alumina; 40 g TPLO (98%) per run; feed rate = 3.0 ml/min (except as noted); catalyst activation temperature = 320° C. (except as noted); reaction temperature = 115° C. (except as noted).
[b]Feed rate = 1.5 ml/min; reaction temperature = 120° C.
[c]Catalyst activation temperature = 200° C.
[d]Catalyst activation temperature = 120° C.

COMPARATIVE EMBODIMENTS A AND B

A pump-around reactor was employed as in Embodiments 1-24, and a Beckman model 110A solvent metering pump was used to pump terpinolene-4,8-oxide (TPLO). The feed/product vessel was a stirred glass reactor which was nitrogen blanketed although the reactor was not under nitrogen. The feed was circulated through the reactor in an upflow mode. An alumina catalyst bed of approximately 10 ml was located in the center section of the reactor. A preheating zone filled with glass beads was used. Catalyst activation was performed in the reactor under vacuum by heating to the desired temperature. Samples were removed from the feed/product vessel at appropriate intervals and analyzed by gas chromatography (GC). Numbers from these GC analyses are reported as area percent and are not otherwise calibrated.

TABLE 2

UPFLOW ISOMERIZATION OF TERPINOLENE OXIDE[a]

| Embodiment | $N_2$ Flow (ml/min) | TPLO Conv. (%) | Reaction Time (hr) | DPNL (%) |
|---|---|---|---|---|
| A | none | 99 | 22 | 79 |
| B | none | 93 | 22 | 77 |

[a]Standard conditions: 6 g of KC-300 alumina; 40 g TPLO (98%) per run; feed rate = 3.0 ml/min (except as noted); catalyst activation temperature = 320° C. (except as noted); reaction temperature = 115° C. (except as noted).

What is claimed is:

1. A process for the isomerization of an epoxide to the corresponding alcohol which comprises isomerizing epoxide in the liquid phase in the presence of a solid alumina catalyst, the isomerization conducted in the downflow mode.

2. A process according to claim 1 wherein the alumina has a relatively low sodium content.

3. A process according to claim 2 wherein the alumina has a sodium content of from about 0% to about 0.5% based upon the weight of the alumina.

4. A process according to claim 2 wherein the sodium content is from about 0% to about 0.1%.

5. A process according to claim 1 wherein the process is conducted in the presence of an inert gaseous diluent.

6. A process according to claim 5 wherein the inert gaseous diluent is nitrogen gas.

7. A process according to claim 6 wherein the alumina has a relatively low sodium content.

8. A process according to claim 1 where the epoxide is a terpenoid epoxide.

9. A process according to claim 8 wherein the epoxide is a tetra-substituted olefin epoxide in which at least one carbon atom of the olefinic group is part of a carbocyclic ring so that the resulting alcohol function is tertiary and attached to the ring.

10. A process according to claim 9 wherein the epoxide is terpinolene-4,8-epoxide.

11. A process according to claim 1 wherein the temperature is in the range of from about 70° C. to about 160° C.

12. A process according to claim 2 wherein the temperature is in the range of from about 110° C. to about 150° C.

13. A process according to claim 1 wherein the alumina catalyst is used in a concentration of from about 1 to about 25 weight percent based on the weight of epoxide.

14. A process according to claim 2 wherein the alumina catalyst is used in a concentration of from about 5 to about 15 weight percent based on the weight of epoxide.

15. A process for increasing the life of a solid alumina catalyst used in the isomerization of an epoxide to the corresponding alcohol which comprises conducting the isomerization in the downflow mode of a liquid epoxide.

16. A process according to claim 15 wherein an inert gaseous diluent is also present in the downflow mode.

17. A process according to claim 16 wherein the alumina catalyst has a relatively low sodium content.

* * * * *